US006417176B2

(12) United States Patent
Houze

(10) Patent No.: US 6,417,176 B2
(45) Date of Patent: Jul. 9, 2002

(54) ARYLSULFONANILIDE PHOSPHATES

(75) Inventor: Jonathan B. Houze, San Mateo, CA (US)

(73) Assignee: Tularik, Inc., South San Francisco, CA (US)

( * ) Notice: Subject to any disclaimer, the term of this patent is extended or adjusted under 35 U.S.C. 154(b) by 0 days.

(21) Appl. No.: 09/779,419

(22) Filed: Feb. 7, 2001

Related U.S. Application Data

(63) Continuation of application No. 09/595,398, filed on Jun. 14, 2000, now Pat. No. 6,211,167, which is a continuation of application No. 09/336,062, filed on Jun. 18, 1999, now abandoned.
(60) Provisional application No. 60/090,681, filed on Jun. 25, 1998.

(51) Int. Cl.[7] .................... A61K 31/675; A61K 31/665; C07F 9/655; C07F 9/6506
(52) U.S. Cl. .......................... 514/80; 514/101; 549/220; 558/190
(58) Field of Search .......................... 549/220; 548/114; 558/190; 514/80, 101

(56) References Cited

U.S. PATENT DOCUMENTS

| 1,955,207 A | 4/1934 | Stotter et al. .................. 167/37 |
| 2,358,365 A | 9/1944 | Tullar ...................... 260/337.6 |
| 2,402,623 A | 6/1946 | Hester et al. ................ 264/556 |
| 3,034,955 A | 5/1962 | Frick et al. .................... 167/37 |
| 4,881,969 A | 11/1989 | Saupe et al. ...................... 71/94 |
| 4,883,914 A | 11/1989 | Alvarado et al. ............. 564/91 |
| 4,900,867 A | 2/1990 | Wilkes et al. ................. 564/91 |
| 5,143,937 A | 9/1992 | Lang et al. .................. 514/603 |
| 5,189,211 A | 2/1993 | Sato et al. ................... 562/430 |
| 5,250,549 A | 10/1993 | Yoshino et al. ............. 514/345 |
| 5,385,931 A | 1/1995 | Bigg et al. ................... 514/443 |
| 5,387,709 A | 2/1995 | Lardy et al. ................ 558/388 |
| 5,529,989 A | 6/1996 | Pettit et al. .................... 514/81 |
| 5,561,122 A | 10/1996 | Pettit .......................... 514/130 |

FOREIGN PATENT DOCUMENTS

| EP | 0 391 799 A | 10/1990 |
| EP | 0 469 901 A | 2/1992 |
| EP | 0 472 449 A | 2/1992 |
| GB | 859 345 A | 1/1961 |
| GB | 938 890 A | 10/1963 |
| GB | 1 189 720 A | 4/1970 |
| GB | 1 242 057 A | 8/1971 |
| GB | 1 306 564 A | 2/1973 |
| WO | WO 97/30677 A2 | 8/1997 |
| WO | 97/30677 | 8/1997 |
| WO | 98/05315 | 2/1998 |
| WO | WO 98/05315 | 2/1998 |

OTHER PUBLICATIONS

Fielding et al, "Synthesis and Reactions of 4–sulpho–2,3,5, 6–Tetrafluorobenzoic Acid"; *Journal of Fluorine Chemistry*, vol. 59, No. 1, pp. 15–31 (1992).

Raibekas et al. "Affinity Probing of Flavin Binding Sites. 2. Identification of Reactive cysteine in the Flavin Domain of *Escherichia coli* DNA Photolyase"; *Biochemistry*, vol. 33, No. 42, pp. 12656–12664 (1994).

Shealy et al. "2–Haloethylating Agents for Cancer Chemotherapy. 2–Haloethyl Sulfonates"; *Journal of Medicinal Chemistry*, vol. 26, pp. 1168–1173 (Aug. 1983).

Olander et al., "A Study of the binding of two sulfonamides to Carbonic Anhydrase"; *Journal of American Chemical Society*, vol. 95, No. 5, pp. 1616–1621 (Mar. 7, 1973).

Hawkinson, et al., "Studies of the Solvolysis of 2–Adamantyl Pentafluorobenzenesulfonate: A $Y_{PFBS}$ Scale"; *The Journal of Organic Chemistry*, Aug. 1988, vol. 53, No. 16, pp. 3857–3860.

Chemical Abstracts, vol. 50, No. 1, Jan. 10, 1956 Colombus, Ohio, US; abstract No. 217g, V.O. Lukashevich: "Sulphonation of halogen–substituted benzene derivatives. formation of anhydrides of corresponding sulphonic acids" col. 217; XP002083056 see abstract & Doklady Akad. Nauk S.S.S.R., vol. 99, 1954, pp. 995–998.

Chemical Abstracts, vol. 74, No. 14, Apr. 5, 1971, Columbus, Ohio, US; abstract No. 65535a, D. Simov, Et al.: "Preparation of azo dyes containing amobile chlorine atom in the benzebe ring" p. 81: XP002083055 see abstract & Izd. Otd. Khim. Nauki, Bulg. Akad. Nauk, vol. 3, No. 1, 1970, pp. 69–82.

I.C. Poppoff, et al.: "Antimalarial agents. 83 Ring–substituted bis–(4–aminophenyl) sulphones and their precursors" *Journal of Medicinal Chemistry*, vol. 14, No. 12, Dec. 1971, pp. 1166–1169, XP002083052 Washington, DC, US see compounds, V, VIII,X, XI, XIII, XVII, XIX, XXVIII, XXXII, XXXVI–XXXVIII, XLI, XLII<XLIV<XLV.

G.E. Chivers, et al.: "Studies in the chemistry of polyhalogenobenzene compounds. The synthesis and reactivity of 2,3,5,6–and 2,3,4,5–tetrachlorobenzenesulphonyl chlorides and related compounds"; *Australian Journal of Chemistry*, vol. 29, No. 7, Jul. 1976, pp. 1572–1582, XP002083174, Melbourne, AU.

(List continued on next page.)

*Primary Examiner*—Floyd D. Higel
*Assistant Examiner*—Kamal Saeed
(74) *Attorney, Agent, or Firm*—Townsend and Townsend and Crew LLP

(57) ABSTRACT

The invention provides compounds, compositions and methods relating to novel arylsulfonanilide derivatives and their use as pharmacologically active agents. The compositions find particular use as pharmacological agents in the treatment of disease states, particularly cancer, psoriasis, vascular restenosis, infections, atherosclerosis and hypercholesterolemia, or as lead compounds for the development of such agents.

38 Claims, No Drawings

OTHER PUBLICATIONS

P.G. DeBenedetti, et al.; "Quantitative structure–activity analysis in dihydropteroate synghase inhibition by sulphones. Comparison with sulphanilamides" *Journal of Medicinal Chemistry*, vol. 30, No. 3, Mar. 1987, pp. 459–464, XP002083053 Washington, DC, US.

V.N. Babushkin, et al.: "Influence of substituents on the frequency of stretching vibrations of sulphur–containing bridging groups in diphenyl systems" *Journal of General Chemistry of the USSR*, vol. 58, No. 7, pt. 2, Jul. 1988., pp. 1457–1460. XP002083054 New York, US.

Yoshimoto and Hansch, "Correlation Analysis of Baker's Studies on Enzyme Inhibition. 2. Chymotrypsin, Thymidine Phosphorylase, Uridine Phosphorylase, Thymidylate Synthetase, Cytosine Nucleoside Deaminase, Dihydrofolate Reductase, malate Dehydrogenase, Glutamate Dehydrogenase, Lactate Dehydrogenase, and Glyceraldehyde–phosphate Dehydrogenase."; *Journal of Medicinal Chemistry* (1976) vol. 19, No. 1 pp. 71–98.

Bai, et al.; "Identification of the cystein Residue of β–Tubulin Alkylated by the Antimitotic Agent 2,4–Dichlorobenzyl Thiocyanate, Facilitated by Separationof the Protein subunits of Tubulin by Hydrophobic column chromatography"; *Biochemistry* 1989, vol. 28, pp. 5606–5612.

ARYLSULFONANILIDE PHOSPHATES

This application is a continuation of and claims benefit of U.S. application Ser. No. 09/595,398, filed Jun. 14, 2000 now patented, U.S. Pat. No. 6,211,167, which is a continuation of U.S. application Ser. No. 09/336,062 filed Jun. 18, 1999 now abandoned, which claims the benefit of U.S. Provisional Patent App. Ser. No. 60/090,681 filed Jun. 25, 1998.

FIELD OF THE INVENTION

The present invention relates to arylsulfonanilide phosphates, derivatives and analogs and their use as pharmacologically active agents-capable of lowering plasma cholesterol levels and inhibiting abnormal cell proliferation.

BACKGROUND

Atherosclerosis is a leading cause of death in the United States. The disease results from excess cholesterol accumulation in the arterial walls, which forms plaques that inhibit blood flow and promote clot formation, ultimately causing heart attacks, stroke and claudication. A principal source of these cholesterol deposits is the low-density lipoprotein (LDL) particles that are present in the blood. There is a direct correlation between LDL concentration and plaque formation in the arteries. LDL concentration is itself largely regulated by the supply of active LDL cell surface receptors, which bind LDL particles and translocate them from the blood into the cell's interior. Accordingly, the upregulation of LDL receptor expression provides an important therapeutic target.

Lipoprotein disorders have been previously called the hyperlipoproteinemias and defined as the elevation of a lipoprotein level above normal. The hyperlipoproteinemias result in elevations of cholesterol, triglycerides or both, and are clinically important because of their contribution to atherosclerotic diseases and pancreatitis.

Lipoproteins are spherical macromolecular complexes of lipid and protein. The lipid constituents of lipoproteins are esterified and unesterified (free) cholesterol, triglycerides, and phospholipids. Lipoproteins transport cholesterol and triglycerides from sites of absorption and synthesis to sites of utilization. Cholesteryl esters and triglycerides are nonpolar and constitute the hydrophobic core of lipoproteins in varying proportions. The lipoprotein surface coat contains the polar constituents —free cholesterol, phospholipids, and apolipoproteins —that permit these particles to be miscible in plasma.

Cholesterol is used for the synthesis of bile acids in the liver, the manufacture and repair of cell membranes, and the synthesis of steroid hormones. There are both exogenous and endogenous sources of cholesterol. The average American consumes about 450 mg of cholesterol each day and produces an additional 500 to 1,000 mg in the liver and other tissues. Another source is the 500 to 1,000 mg of biliary cholesterol that is secreted into the intestine daily; about 50 percent is reabsorbed (enterohepatic circulation). The rate-limiting enzyme in endogenous cholesterol synthesis is 3-hydroxy-3-methylglutaryl coenzyme A (HMG-CoA) reductase. Triglycerides, which are nonpolar lipids consisting of a glycerol backbone and three fatty acids of varying length and degrees of saturation, are used for storage in adipose tissue and for energy.

Lipoproteins are classified into groups based upon size, density, electrophoretic mobility, and lipid and protein composition. Very low density lipoproteins (VLDL) are large, triglyceride-rich lipoproteins that are synthesized and secreted by hepatocytes. VLDL interacts with lipoprotein lipase in capillary endothelium, and the core triglycerides are hydrolyzed to provide fatty acids to adipose and muscle tissue. About half of the catabolized VLDL particles are taken up by hepatic LDL receptors and the other half remain in plasma, becoming intermediate-density lipoprotein (IDL). IDL is enriched in cholesteryl esters relative to triglycerides and is gradually converted by hepatic triglyceride lipase to the smaller, denser, cholesterol ester-rich LDL. As IDL is converted to LDL, apolipoprotein E becomes detached, and only one apolipoprotein remains, apo B-100.

LDL normally carries about 75 percent of the circulating cholesterol. Cellular LDL uptake is mediated by a glycoprotein receptor molecule that binds to apo B-100. Approximately 70 percent of LDL is cleared by receptor uptake, and the remainder is removed by a scavenger cell pathway using nonreceptor mechanisms. The LDL receptors span the thickness of the cell's plasma membrane and are clustered in specialized regions where the cell membrane is indented to form craters called coated pits. These pits invaginate to form coated vesicles, where LDL is separated from the receptor and delivered to a lysosome so that digestive enzymes can expose the cholesteryl ester and cleave the ester bond to form free cholesterol. The receptor is recycled to the cell surface.

As free cholesterol liberated from LDL accumulates within cells, there are three important metabolic consequences. First, there is a decrease in the synthesis of HMG-CoA reductase, the enzyme that controls the rate of de novo cholesterol biosynthesis by the cell. Second, there is activation of the enzyme acyl cholesterol acyltransferase (ACAT), which esterifies free cholesterol into cholesterol ester, the cell's storage form of cholesterol. Third, accumulation of cholesterol suppresses the cell's synthesis of new LDL receptors. This feedback mechanism reduces the cell's uptake of LDL from the circulation.

Lipoproteins play a central role in atherosclerosis. This association with the most common cause of death in the developed world defines the principal clinical importance of the hyperlipoproteinemias. Individuals with an elevated cholesterol level are at higher risk for atherosclerosis. Multiple lines of evidence, including epidemiological, autopsy, animal studies and clinical trials, have established that LDL is atherosclerogenic and that the higher the LDL level, the greater the risk of atherosclerosis and its clinical manifestations. A certain degree of LDL elevation appears to be a necessary factor in the development of atherosclerosis, although the process is modified by many other factors (e.g., blood pressure, tobacco use, blood glucose level, antioxidant level, and clotting factors). Acute pancreatitis is another major clinical manifestation of dyslipoproteinemia. It is associated with chylomicronemia and elevated VLDL levels. Most patients with acute pancreatitis have triglyceride levels above 2,000 mg/dL, but a 1983 NIH consensus development conference recommended that prophylactic treatment of hypertriglyceridemia should begin when fasting levels exceed 500 mg/dL. The mechanism by which chylomicronemia and elevated VLDL levels cause pancreatitis is unclear. Pancreatic lipase may act on triglycerides in pancreatic capillaries, resulting in the formation of toxic fatty acids that cause inflammation.

Abundant evidence indicates that treatment of hyperlipoproteinemia will diminish or prevent atherosclerotic complications. In addition to a diet that maintains a normal body weight and minimizes concentrations of lipids in plasma, therapeutic agents that lower plasma concentrations of lipoproteins, either by diminishing the production of lipoproteins or by enhancing the efficiency of their removal from plasma, are clinically important.

The most promising class of drugs currently available for the treatment of hyperlipoproteinemia or hypercholesterolemia acts by inhibiting HMG-CoA reductase, the rate-limiting enzyme in endogenous cholesterol synthesis. Drugs of this class competitively inhibit the activity of the enzyme. Eventually, this inhibition leads to a decrease in the endogenous synthesis of cholesterol and by normal homeostatic mechanisms, plasma cholesterol is taken up by LDL receptors to restore the intracellular cholesterol balance.

Through both the release of precursors of LDL and receptor-mediated LDL uptake from the serum, liver cells play a critical role in maintaining serum cholesterol homeostasis. In both man and animal models, an inverse correlation appears to exist between liver LDL receptor expression levels and LDL-associated serum cholesterol levels. In general, higher hepatocyte LDL receptor numbers result in lower LDL-associated serum cholesterol levels. Cholesterol released into hepatocytes can be stored as cholesteryl esters, converted into bile acids and released into the bile duct, or it can enter into an oxycholesterol pool. It is this oxycholesterol pool that is believed to be involved in end product repression of both the genes of the LDL receptor and enzymes involved in the cholesterol synthetic pathway.

Transcription of the LDL receptor gene is known to be repressed when cells have an excess supply of cholesterol, probably in the form of oxycholesterol. A DNA sequence in the LDL receptor promoter region, known as the sterol response element (SRE), appears to confer this sterol end product repression. This element has been extensively investigated (Brown, Goldstein and Russell, U.S. Pat. Nos. 4,745,060 and 4,935,363). The SRE can be inserted into genes that normally do not respond to cholesterol, conferring sterol end product repression of the chimeric gene. The exact mechanism of the repression is not understood. Brown and Goldstein have disclosed methods for employing the SRE in a screen for drugs capable of stimulating cells to synthesize LDL receptors (U.S. Pat. No. 4,935,363). It would be most desirable if the synthesis of LDL receptors could be upregulated at the level of gene expression. The upregulation of LDL receptor synthesis at this level offers the promise of resetting the level of serum cholesterol at a lower, and clinically more desirable, level. Presently, however, there are no cholesterol lowering drugs that are known to operate at the level of gene expression. The present invention describes methods and compounds that act to inhibit directly or indirectly the repression of the LDL receptor gene, resulting in induction of the LDL receptor on the surface of liver cells, facilitating LDL uptake, bile acid synthesis and secretion to remove cholesterol metabolites and hence the lowering of LDL-associated serum cholesterol levels.

A number of human diseases stem from processes of uncontrolled or abnormal cellular proliferation. Most prevalent among these is cancer, a generic name for a wide range of cellular malignancies characterized by unregulated growth, lack of differentiation, and the ability to invade local tissues and metastasize. These neoplastic malignancies affect, with various degrees of prevalence, every tissue and organ in the body. A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disruptors (e.g., vincristine, vinblastine, paclitaxel), DNA intercalators (e.g., doxorubicin, daunomycin, cisplatin), and hormone therapy (e.g., tamoxifen, flutamide). The ideal antineoplastic drug would kill cancer cells selectively, with a wide therapeutic index relative to its toxicity towards non-malignant cells. It would also retain its efficacy against malignant cells even after prolonged exposure to the drug. Unfortunately, none of the current chemotherapies possess an ideal profile. Most possess very narrow therapeutic indexes, and in practically every instance cancerous cells exposed to slightly sublethal concentrations of a chemotherapeutic agent will develop resistance to such an agent, and quite often cross-resistance to several other antineoplastic agents.

Psoriasis, a common chronic skin disease characterized by the presence of dry scales and plaques, is generally thought to be the result of abnormal cell proliferation. The disease results from hyperproliferation of the epidermis and incomplete differentiation of keratinocytes. Psoriasis often involves the scalp, elbows, knees, back, buttocks, nails, eyebrows, and genital regions, and may range in severity from mild to extremely debilitating, resulting in psoriatic arthritis, pustular psoriasis, and exfoliative psoriatic dermatitis. No therapeutic cure exists for psoriasis. Milder cases are often treated with topical corticosteroids, but more severe cases may be treated with antiproliferative agents, such as the antimetabolite methotrexate, the DNA synthesis inhibitor hydroxyurea, and the microtubule disrupter colchicine.

Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic-agents per se (e.g. bacteria, trypanosomes, fungi, etc) are also subject to selective proliferative control using the subject compositions and compounds.

Accordingly, it is one object of the present invention to provide compounds which directly or indirectly upregulate LDL receptor synthesis at the level of gene expression and are useful in the treatment of hypercholesterolemia or hyperlipoproteinemia.

A further object of the present invention is to provide therapeutic compositions for treating said conditions.

A further object of the invention is to provide therapeutic compositions for treating pancreatitis.

Still further objects are to provide methods for upregulating LDL receptor synthesis, for lowering serum LDL cholesterol levels, and for preventing and treating atherosclerosis.

A further object of the present invention is to provide compounds which directly or indirectly are toxic to actively dividing cells and are useful in the treatment of cancer, viral and bacterial infections, vascular restenosis, inflammatory diseases, autoimmune diseases, and psoriasis.

A further object of the present invention is to provide therapeutic compositions for treating said conditions.

Still further objects are to provide methods for killing actively proliferating cells, such as cancerous, bacterial, or epithelial cells, and treating all types of cancers, infections, inflammatory, and generally proliferative conditions. A further object is to provide methods for treating other medical conditions characterized by the presence of rapidly proliferating cells, such as psoriasis and other skin disorders.

Other objects, features and advantages will become apparent to those skilled in the art from the following description and claims.

SUMMARY OF THE INVENTION

The invention provides novel arylsulfonanilide phosphate compounds, as well as methods and compositions relating to novel arylsulfonanilide phosphates and their use as pharmacologically active agents. The compounds and compositions find use as pharmacological agents in the treatment of disease states, particularly hypercholesterolemia, atherosclerosis, cancer, bacterial infections, and psoriasis, or as lead compounds for the development of such agents. The compounds of the invention have the formula:

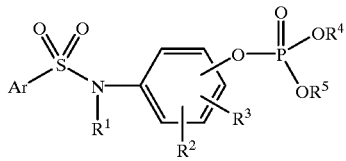

or a pharmaceutically acceptable salt thereof.

In the above formula, the symbol $R^1$ represents a hydrogen, $(C_1-C_6)$alkyl or $(C_1-C_6)$heteroalkyl. The symbols $R^2$ and $R^3$ are each independently hydrogen, halogen, $(C_1-C_8)$alkyl, $(C_1-C_8)$heteroalkyl, —$OR^{11}$ or —$NR^{11}R^{12}$, in which the symbols $R^{11}$ and $R^{12}$ each independently represent hydrogen, $(C_1-C_8)$alkyl or $(C_1-C_8)$heteroalkyl. Alternatively, $R^2$ and $R^3$, when attached to adjacent carbon atoms, can be linked together to form a fused 5-, 6- or 7-membered ring.

The symbols $R^4$ and $R^5$ each independently represent hydrogen, $(C_1-C_8)$alkyl, $(C_1-C_8)$heteroalkyl, aryl, heteroaryl, aryl$(C_1-C_4)$alkyl, aryl$(C_1-C_4)$heteroalkyl, heteroaryl$(C_1-C_4)$alkyl and heteroaryl$(C_1-C_4)$heteroalkyl. Optionally, $R^4$ and $R^5$ are linked together to form a 5-, 6- or 7-membered ring. Additionally, $R^4$ can also represent a single bond to the phenyl ring bearing the phosphoryl group. When $R^4$ is a single bond to the phenyl ring, $R^5$ is hydrogen, $(C_1-C_8)$alkyl, $(C_1-C_8)$heteroalkyl, aryl, heteroaryl, aryl $(C_1-C_4)$alkyl, aryl$(C_1-C_4)$heteroalkyl, heteroaryl$(C_1-C_4)$ alkyl or heteroaryl$(C_1-C_4)$heteroalkyl.

The symbol Ar represents a substituted aryl group selected from the group of:

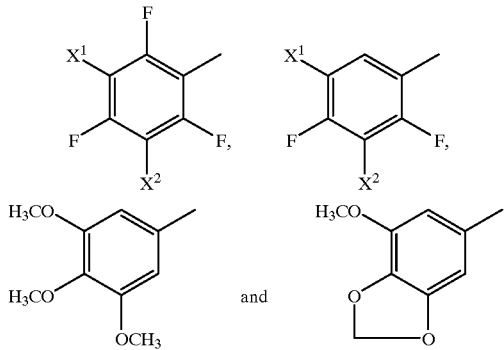

in which $X^1$ and $X^2$ are each independently F, Cl or Br.

The methods of the present invention use pharmaceutical compositions containing compounds of the foregoing description of the general Formula I for the treatment of pathology such as cancer, bacterial infections, psoriasis, hypercholesterolemia, atherosclerosis, pancreatitis, and hyperlipoproteinemia. Briefly, the inventions involve administering to a patient an effective formulation of one or more of the subject compositions.

DETAILED DESCRIPTION OF THE INVENTION

Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multi- radicals, having the number of carbon atoms designated (i.e. $C_1-C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1-and 3- propynyl, 3-butynyl, and the higher homologs and isomers. The term "alkyl," unless otherwise noted, is also meant to include those derivatives of alkyl defined in more detail below as "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "alkoxy," employed alone or in combination with other terms means, unless otherwise stated, an alkyl group, as defined above, connected to the remainder of the molecule via an oxygen atom, such as, for example, methoxy, ethoxy, 1-propoxy, 2-propoxy and the higher homologs and isomers.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N ($CH_3$)—$CH_3$, —$CH_2$—S—$CH_2$—$CH_3$, —$CH_2$—$CH_2$—S (O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini. Still further, for alkylene and heteroalkylene linking groups, as well as all other linking groups described herein, no specific orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a carbon atom or a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzinidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

The terms "arylalkyl" and "arylheteroalkyl" are meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 1-naphthyloxy-3-propyl, and the like). The arylalkyl and arylheteroalkyl groups will typically contain from 1 to 3 aryl moieties attached to the alkyl or heteroalkyl portion by a covalent bond or by fusing the ring to, for example, a cycloalkyl or heterocycloalkyl group. For arylheteroalkyl groups, a heteroatom can occupy the position at which the group is attached to the remainder of the molecule. For example, the term "arylheteroalkyl" is meant to include benzyloxy, 2-phenylethoxy, phenethylamine, and the like.

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', —halogen, —SiR'R"R'", —OC(O)R', —CO$_2$R', —CONR'R", —OC(O)NR'R", —NR"C(O)R', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical. R', R" and R'" each independently refer to hydrogen, unsubstituted($C_1$–$C_8$)alkyl and heteroalkyl, unsubstituted aryl, aryl substituted with 1–3 halogens, unsubstituted alkyl, alkoxy or thioalkoxy groups, or aryl—($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl.

Similarly, substituents for the aryl groups are varied and are selected from: —halogen, —OR', —OC(O)R', —NR'R", —SR', —R', —CN, —NO$_2$, —CO$_2$R', —CONR'R", —OC(O)NR'R", —NR"C(O)R', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R' and R" are independently selected from hydrogen, ($C_1$–$C_8$)alkyl and heteroalkyl, unsubstituted aryl, (unsubstituted aryl)-($C_1$–$C_4$) alkyl, and (unsubstituted aryl)oxy-($C_1$-$C_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula I. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

The compounds described herein are related to compounds provided in PCT publications WO 97/30677 and WO 98/05315. More particularly, compounds are now described having an attached phosphate, phosphate salt, or phosphate ester group. These arylsulfonanilide phosphates are less lipophilic that the corresponding arylsulfonanilide phenols and are expected to reduce brain concentrations of the phenol when administered as a bolus intravenously. Without intending to be bound by any particular theory, it was believed that the compounds would be readily hydrolyzed in vivo to provide the phenol as the active species. However, the compounds of the present invention have demonstrated surprising stability in cell culture media, dosing solution, and mouse plasma, yet provide a level of efficacy against a tumor model equivalent to the parent phenol (non-phosporylated compound) which appears to be present in an amount of only about 4–10% (based on the administered arylsulfonanilide phosphate). Additionally, the arylsulfonanilide phosphates provide a bulk stability, or improved shelf-life, relative to the parent phenols.

Embodiments of the Invention

The present invention provides novel arylsulfonanilide phosphate derivatives having the formula:

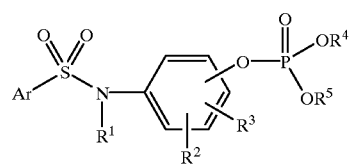

I in which the symbol $R^1$ represents hydrogen, $(C_1-C_6)$alkyl or $(C_1-C_6)$heteroalkyl, preferably hydrogen.

The symbols $R^2$ and $R^3$ are each independently hydrogen, halogen, $(C_1-C_8)$alkyl, $(C_1-C_8)$heteroalkyl, —$OR^{11}$ or —$NR^{11}R^{12}$, in which $R^{11}$ and $R^{12}$ are each independently hydrogen, $(C_1-C_8)$alkyl or $(C_1-C_8)$heteroalkyl. Additionally, when $R^2$ and $R^3$ are attached to adjacent carbon atoms, they can be linked together to form a fused 5-, 6- or 7-membered ring. In preferred embodiments, $R^2$ and $R^3$ occupy positions on the phenyl ring that are meta and/or para to the sulfonanilide nitrogen. More preferably, $R^2$ represents hydrogen, $(C_1-C_3)$alkyl or $(C_1-C_3)$alkoxy. In other preferred embodiments, $R^3$ represents hydrogen, $(C_1-C_3)$alkyl, —$OR^{11}$ or —$NR^{11}R^{12}$, wherein $R^{11}$ and $R^{12}$ are each independently hydrogen, $(C_1-C_3)$alkyl or $(C_1-C_3)$heteroalkyl The symbols $R^4$ and $R^5$ are each independently hydrogen, $(C_1-C_8)$alkyl, $(C_1-C_8)$heteroalkyl, aryl, heteroaryl, aryl$(C_1-C_4)$alkyl, aryl$(C_1-C_4)$heteroalkyl, heteroaryl$(C_1-C_4)$alkyl or heteroaryl$(C_1-C_4)$heteroalkyl. In one group of embodiments, $R^4$ and $R^5$ are optionally linked together to form a 5-, 6- or 7-membered ring. Alternatively, $R^4$ represents a single bond to the phenyl ring bearing the phosphoryl group and $R^5$ is hydrogen, $(C_1-C_8)$alkyl, $(C_1-C_8)$heteroalkyl, aryl, heteroaryl, aryl$(C_1-C_4)$alkyl, aryl$(C_1-C_4)$heteroalkyl, heteroaryl$(C_1-C_4)$alkyl and heteroaryl$(C_1-C_4)$heteroalkyl.

The symbol Ar is a substituted aryl group selected from:

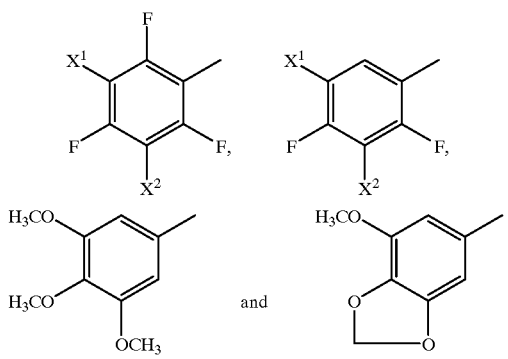

in which $X^1$ and $X^2$ are each independently selected from F, Cl and Br.

In one group of preferred embodiments, Ar is pentafluorophenyl. In another group of preferred embodiments, Ar is 2,3,4,5-tetafluorophenyl. In yet another group of preferred embodiments, Ar is 3,4,5-trimethoxyphenyl. In still another group of preferred embodiments, Ar is 3-methoxy4,5-methylenedioxyphenyl.

In addition to the generally preferred substituents provided above, a number of particular formulae are also preferred. One preferred group of compounds are represented by the formula:

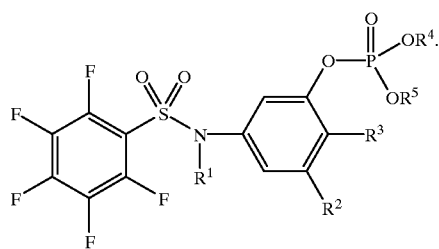

Ia

In this group of embodiments, $R^1$–$R^5$ can be any of the groups described above. Preferably, $R^1$ is hydrogen. $R^2$ is preferably hydrogen, $(C_1$–$C_3)$alkyl or $(C_1$–$C_3)$alkoxy, and $R^3$ is preferably hydrogen, $(C_1$–$C_3)$alkyl, —$OR^{11}$ or —$NR^{11}R^{12}$, wherein $R^{11}$ and $R^{12}$ are each independently hydrogen, $(C_1$–$C_3)$alkyl or $(C_1$–$C_3)$heteroalkyl.

In another group of preferred embodiments, the compounds have the formula:

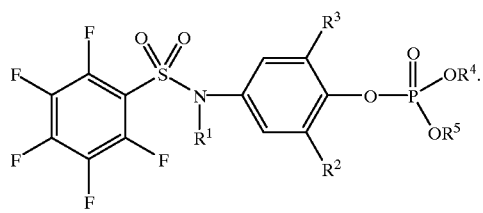

Ib

In this group of embodiments, as with those immediately above, $R^1$–$R^5$ can be any of the groups described for formula I. Preferably, $R^1$ is hydrogen, $R^2$ is hydrogen, $(C_1$–$C_3)$alkyl or $(C_1$–$C_3)$alkoxy, and $R^3$ is hydrogen, $(C_1$–$C_3)$alkyl, —$OR^{11}$ or —$NR^{11}R^{12}$, wherein $R^{11}$ and $R^{12}$ are each independently hydrogen, $(C_1$–$C_3)$alkyl or $(C_1$–$C_3)$ heteroalkyl. In the most preferred embodiments, $R^1$ is hydrogen, $R^2$ is hydrogen and $R^3$ is methoxy, methyl, dimethylamino or hydroxy. $R^4$ and $R^5$ are preferably hydrogen, $(C_1$–$C_3)$alkyl or aryl.

In yet another group of preferred embodiments, the compounds have the formula:

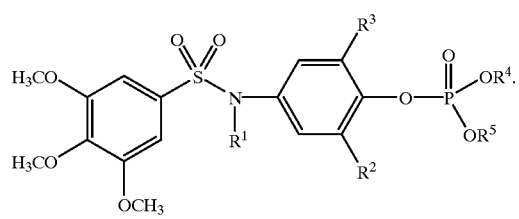

Ic

In this group of embodiments, the preferred substituents are the same as those described for formula Ib.

In still another group of preferred embodiments, the compounds have the formula:

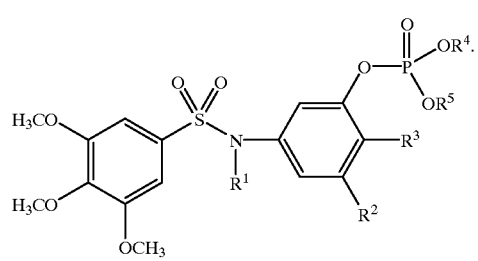

Id

In this group of embodiments, the preferred substituents-are the same as those described for formula Ib.

In still another group of preferred embodiments, the compounds have the general formula I in which $R^2$ and $R^3$ are combined to form a fused 5-member ring. Preferred compounds in this group of embodiments are exemplified by the compounds:

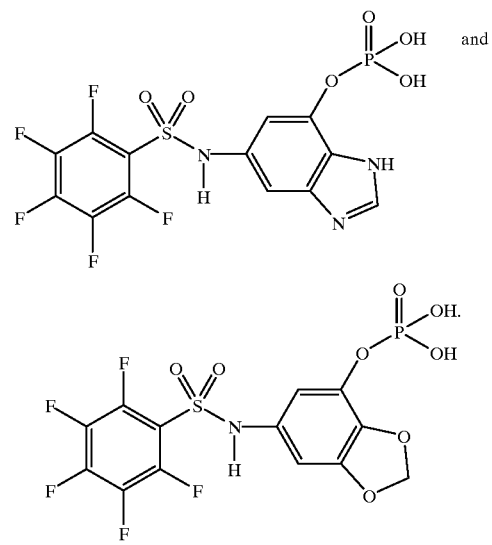

Synthesis

Compounds of the present invention can be prepared using certain intermediates and methods described in WO 97/30677 and WO 98/05315. In one group of embodiments, arylsulfonamidophenols can be prepared as described, and the phenolic hydroxy group can then be phosphorylated using reagents such as diethylphosphorylchloride or dimethylphosphorylchloride. Additional compounds can be prepared via ester exchange or saponification.

Still other phosphorylation procedures useful in preparing the present compounds are described in Silverberg, et al., *Tetrahedron Lett.* 37(6):771–774 (1996), Saulnier, et al., *Bioorg. Med. Chem. Lett.* 4:2567–2572 (1994), and U.S. Pat. No. 5,561,122, the disclosures of each being incorporated herein by reference.

The compounds used as initial starting materials in this invention may be purchased from commercial sources or alternatively are readily synthesized by standard procedures which are well know to those of ordinary skill in the art.

Some of the compounds of Formula I may exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography, repeated recrystallization of derived asymmetric salts, or derivatization, which techniques are well known to those of ordinary skill in the art.

The compounds of the invention may be labeled in a variety of ways. For example, the compounds may contain radioactive isotopes such as, for example, $^3$H (tritium) and $^{14}$C (carbon-14). Similarly, the compounds may be advantageously joined, covalently or noncovalently, directly or through a linker molecule, to a wide variety of other compounds, which may provide pro-drugs or function as carriers, labels, adjuvents, coactivators, stabilizers, etc. Such labeled and joined compounds are contemplated within the present invention.

Analysis of Compounds

Representative compounds and compositions were demonstrated to have pharmacological activity in in vitro and in vivo assays, e.g., they are capable of specifically modulating a cellular physiology to reduce an associated pathology or provide or enhance a prophylaxis.

Certain preferred compounds and compositions are capable of specifically regulating LDL receptor gene expression. Compounds may be evaluated in vitro for their ability to increase LDL receptor expression using western-blot analysis, for example, as described in Tam et al. (*J. Biol Chem.* 1991, 266, 16764). Established animal models to evaluate hypocholesterolemic effects of compounds are known in the art. For example, compounds disclosed herein are shown to lower cholesterol levels in hamsters fed a high-cholesterol diet, using a protocol similar to that described in Spady et al. (*J. Clin. Invest.* 1988, 81, 300), Evans et al. (*J. Lipid Res.* 1994, 35, 1634), and Lin et al (*J. Med Chem.* 1995, 38, 277).

Certain preferred compounds and compositions display specific toxicity to various types of cells. Certain compounds and compositions of the present invention exert their cytotoxic effects by interacting with cellular tubulin. For certain preferred compounds and compositions of the present invention, that interaction is covalent and irreversible. Compounds and compositions may be evaluated in vitro for their ability to inhibit cell growth, for example, as described in Ahmed et al. (*J. Immunol Methods* 1994, 170, 211). Established animal models to evaluate antiproliferative effects of compounds are known in the art. For example, compounds can be evaluated for their ability to inhibit the growth of human tumors grafted into immunodeficient mice using methodology similar to that described by Rygaard and Povlsen (*Acta Pathol. Microbiol. Scand.* 1969, 77, 758) and Giovanella and Fogh (*Adv. Cancer Res.* 1985, 44, 69).

Formulation and Administration of Compounds and Pharmaceutical Compositions

The invention provides methods of using the subject compounds and compositions to treat disease or provide medicinal prophylaxis, to upregulate LDL receptor gene expression in a cell, to reduce blood cholesterol concentration in a host, to slow down and/or reduce the growth of tumors, etc. These methods generally involve contacting the cell with or administering to the host an effective amount of the subject compounds or pharmaceutically acceptable compositions.

The compositions and compounds of the invention and the pharmaceutically acceptable salts thereof can be administered in any effective way such as via orals parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically converted to the subject compound by the recipient host. A wide variety of pro-drug formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other hypocholesterolemic or antiproliferative therapeutic or prophylactic agents, different from the subject compounds. In many instances, administration in conjunction with the subject compositions enhances the efficacy of such agents. Examplary antiproliferative agents include cyclophosphamide, methotrexate, adriamycin, cisplatin, daunomycin, vincristine, vinblastine, vinarelbine, paclitaxel, docetaxel, tamoxifen, flutamide, hydroxyurea, and mixtures thereof. Exemplary hypocholesterolemic and/or hypolipemic agents include: bile acid sequestrants such as quaternary amines (e.g. cholestyramine and colestipol); nicotinic acid and its derivatives; HMG-CoA reductase inhibitors such as mevastatin, pravastatin, and simvastatin; gemfibrozil and other fibric acids, such as gemfibrozil, clofibrate, fenofibrate, benzafibrate and cipofibrate; probucol; raloxifene and its derivatives; and mixtures thereof.

The compounds and compositions also find use in a variety of in vitro and in vivo assays, including diagnostic assays. For example, various allotypic LDL receptor gene expression processes may be distinguished in sensitivity assays with the subject compounds and compositions, or panels thereof. In certain assays and in in vivo distribution studies, it is desirable to used labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples are offered by way of illustration and not by way of limitation.

EXAMPLES $^1$H-NMR spectra were recorded on a Varian Gemini 400 MHz NMR spectrometer. Significant peaks are tabulated in the order number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses).

Preparation of Synthetic Intermediates

The majority of the starting materials for the synthesis of the examples of the present invention are available from commercial sources or are known compounds described in the published literature. Literature references of general utility to the following examples include:

1) *Organic Syntheses, Coll. Vol. VII;* 1990, Jeremiah P. Freeman, ed., John Wiley & Sons, 508–511.

2) Robson, P., Smith, T. A., Stephens, R., Tatlow, J., *J. Chem. Soc.,* 1963, 3692–3703.

3) *Synthesis of Fluoroorganic Compounds;* 1985, Knunyants, I. and Yakobson, G., eds., Springer-Verlag, 190.

The synthesis of a selected group of starting materials is exemplified as follows in Examples A–K:

Example A

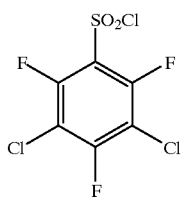

3,5-Dichloro-2,4,6-trifluorophenylsulfonyl chloride.

1,3-Dichloro-2,4,6-trifluorobenzene (5.0 g, 25 mmol) and chlorosulfonic acid (10.0 mL, 150 mmol) were mixed at ambient temperature under a nitrogen atmosphere and the reaction was heated at 80° C. for 24 h. The mixture was then allowed to cool to ambient temperature and was poured onto 12 g of crushed ice. The product was extracted with diethyl ether, dried over MgSO$_4$, and the solvent was evaporated to produce 4.9 g of the title compound, which was used without further purification. MS (EI): 300 (30, M$^+$), 298 (28), 263 (100), 199 (80).

Examples B and C

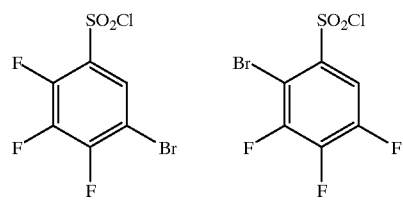

5-Bromo-2,3,4-trifluorophenylsulfonyl chloride (Example B) and 2-Bromo-3,4,5-trifluorophenylsulfonyl chloride (Example C).

The title compounds were obtained as a mixture from 1-bromo-2,3,4-trifluorobenzene by a method similar to that used in Example A.

Example D

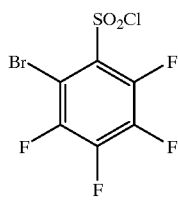

2-Bromo-3,4,5,6-tetrafluorophenylsulfonyl chloride.

1-Bromo-2,3,4,5-tetrafluorobenzene (5.0 g, 21.8 mmol) was mixed at ambient temperature with 20% fuming sulfuric acid (20 mL). The mixture was heated at 40° C. for 3 h and at 110° C. for 2 h. The reaction mixture was allowed to cool to ambient temperature and poured onto 12 g of crushed ice. The mixture was acidified dropwise with concentrated HCl (2 mL) until a solid, consisting mostly of 2-bromo-3,4,5,6-tetrafluorophenylsulfonic acid was formed. The solid was filtered, washed with 12N HCl, and dried under high vacuum to afford 5.3 g of 2-bromo-3,4,5,6-tetrafluorophenylsulfonic acid as a white hygroscopic solid that was used without further purification. To the sulfonic acid (3.0 g, 9.7 mmol) was then added phosphorous pentachloride (8.0 g, 38.4 mmol) in small portions, at ambient temperature (Caution: exothermic reaction with significant evolution of HCl). The reaction was allowed to stir for 20 minutes after the final addition of phosphorous pentachloride. The reaction mixture was then poured onto crushed ice and the white solid that formed was filtered and dried to afford 2.8 g of the title compound, which was used without further purification. MS (EI): 328 (30, M$^+$), 293 (70), 229 (30), 148 (100).

Example E

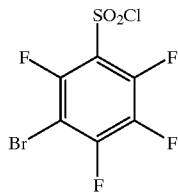

3-Bromo-2,4,5,6-tetrafluorophenylsulfonyl chloride.

The title compound was synthesized from 1-bromo-2,3,4,6-tetrafluorobenzene by a method similar to that used in Example D. MS (EI): 328 (20, M$^+$), 293 (70), 229 (50), 148 (100).

Example F

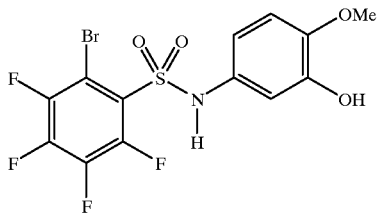

1-Bromo-3,4,5,6-tetrafluoro-2-[(3-hydroxy-4-methoxyphenyl)amino-sulfonyl]benzene.

The title compound was prepared in a manner similar to that described in Example 6 of WO 97/30677, beginning with 3-hydroxy4methoxyaline and 2-bromo-3,4,5,6-tetrafluorophenylsulfonyl chloride (Example D, above). $^1$H-NMR (CDCl$_3$): δ 7.28 (br s, 1H), 6.69 (m, 3H), 5.72 (s, 1H), 3.82 (s, 3H). MS (EI): 431 (20), 429 (20), 138 (100). Anal. calcd. for C$_{13}$H$_8$BrF$_4$NO$_4$S: C, 36.30; H, 1.87; N, 3.26; S, 7.45. Found: C, 36.20; H, 1.90; N, 3.31; S, 7.39.

Example G

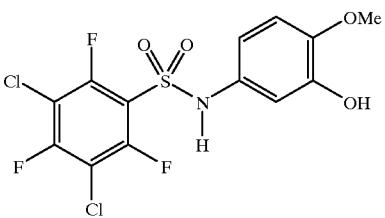

1,3-Dichloro-2,4,6-trifluoro-5-[(3-hydroxy-4-methoxyphenyl)amino-sulfonyl]benzene.

The title compound was prepared in a manner similar to that described in Example 6 of WO 97/3-677, beginning with 3-hydroxy-4-methoxyaline and 3,5-dichloro-2,4,6-trifluorophenylsulfonyl chloride (Example A, above). $^1$H-NMR (CDCl$_3$): δ 6.88 (1H, br s), 6.7–6.8 (3H, m), 5.66 (1H, s), 3.85 (3H, s). MS(EI): 402 (15, M$^+$), 401 (20), 138 (100). Anal. Calcd. for C$_{13}$H$_8$Cl$_2$F$_3$NO$_4$S: C, 38.83; H, 2.00; N, 3.48; S. 7.97. Found: C, 38.66; H, 1.97; N, 3.39; S, 7.86.

Example H

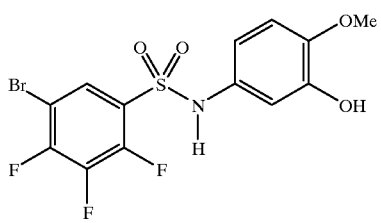

1-Bromo-2,3,4-trifluoro-5-[(3-hydroxy-4-methoxyphenyl)amino-sulfonyl]benzene.

1-Bromo-2,3,4-trifluoro-5-[(3-hydroxy-4-methoxyphenyl)amino-sulfonyl]benzene and 1-Bromo-4,5,6-trifluoro-2-[(3-hydroxy-4-methoxyphenyl)amino-sulfonyl]benzne were prepared in a manner similar to that described above, beginning with a mixture of 5-bromo-2,3,4-trifluorophenylsulfonyl chloride (Example B) and 2-bromo-3,4,5-trifluorophenylsulfonyl chloride (Example C) and 3-hydroxy4-methoxyaniline. The two isomeric compounds were separated by column chromatography (silica gel; ethyl acetate:hexanes, 1:4). $^1$H-NMR (CDCl$_3$): δ 7.79 (1H, m), 6.72–6.62 (4H, m), 5.65 (1H, s), 3.85 (3H, s).

Example I

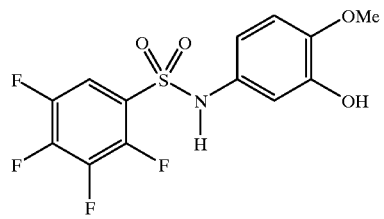

2,3,4,5-Tetrafluoro- 1-[(3-hydroxy-4-methoxyphenyl)aminosulfonyl]benzene.

The title compound was prepared via catalytic hydrogenation of the compound prepared in Example F above. Briefly, the starting material was in methanol and placed in a closed vessel. A catalytic amount of 10% Pd/charcoal was added and the mixture was hydrogenated at 60 psi H$_2$ for 4 h. The resulting mixture was filtered through celite, the solvent was evaporated and the residue was purified by chromatography (silica; EtOAc/Hexane, 1:4) to yield the title compound. $^1$H-NMR (CDCl$_3$): δ 7.43 (1H, m), 6.80 (1H, br s), 6.73–6.60 (3H, m), 5.67 (1H, s), 3.84 (3H, s). MS(EI): 351 (20, M$^+$), 138 (100). Anal. Calcd. for C$_{13}$H$_9$F$_4$NO$_4$S: C, 44.45; H, 2.58; N, 3.99; S, 9.13. Found: C, 44.39; H, 2.59; N, 3.94; S, 9.24.

Preparation of other intermediate benzenesulfonamidophenols are described in WO 97/30677 and WO 98/05315. For example, 2-hydroxy- 1-methoxy4-pentafluorophenyl-sulfonarnidobenzene (Example 6, page 33); 3-hydroxy-1-pentafluorophenyl-sulfonamidobenzene (Example 9, page 34): 4hydroxy-1-pentafluorophenyl-sulfonarnidobenzene (Example 10, page 35); 1,3-dimethoxy-2-hydroxy-5-pentafluoro-phenylsulfonardobenzene (Example 27, page 45); and 3-hydroxy-5-methoxy-1- pentafluorophenyl-sulfonamidobenzene (Example 28, page 46) are described in each of the cited PCT publications.

Example J

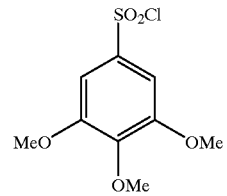

3,4,5-Trimethoxybenzenesulfonyl Chloride.

3,4,5-Trimethoxybenzenesulfonyl chloride was synthesized from 3,4,5-trimethoxyaniline according to the procedure described in G. Pifferi and R. Monguzzi, *Journal of Pharmaceutical Sciences*, 1973, 62, 1393. In this procedure the aniline was dissolved in concentrated hydrochloric acid and to the resulting mixture was added a solution of aqueous sodium nitrite at 0° C, the resulting mixture containing the desired diazonium salt was added at 5° C. to a saturated solution of sulfur dioxide in glacial acetic acid containing substoichiometric amount of cuprous chloride. The mixture was stirred at ambient temperature for 3 h, poured into cold water, and the product extracted with dichloromethane. The solvent was evaporated and the solid residue was recrystallized from hexanes.

Example K

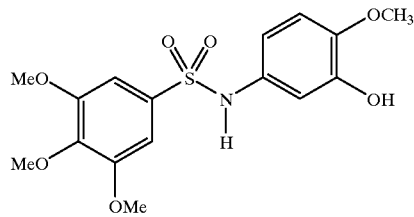

1-[(3-Hydroxy-4-methoxyphenyl)aminosulfonyl]-3,4,5-trimethoxybenzene

To a solution of 3,4,5-trimethoxybenzenesulfonyl chloride (500 mg, 1.88 mmol) in methanol (10 mL) was added 3-hydroxy4-methoxyaniline (523 mg, 3.76 mmol) at ambient temperature. After stirring for 1 h, the reaction mixture was concentrated and the crude residue was purified by chromatography over silica to afford 430 mg (62%) of product as fine white needles, m.p. 145–146° C. $^1$H-NMR (CDCl$_3$): δ 9.74 (1H, s), 9.15 (1H, s), 6.98 (2H, s), 6.78 (1H, d, J=8.8 Hz), 6.63 (1H, d, J=2.6 Hz), 6.50 (1H, dd, J=8.8, 2.6 Hz), 3.76 (6H, s), 3.70 (3H, s), 3.68 (3H, s). Anal. Calcd. for $C_{16}H_{19}N_1O_7S$: C, 52.03; H, 5.18; N, 3.79; S, 8.68. Found: C, 51.87; H, 5.28; N, 3.76; S, 8.77. Each of the phenols above, as well as the related members having different substitution patterns can be phosphorylated using known methods including the procedure described in detail in Example 1.

EXAMPLE 1

This example illustrates the phosphorylation of the 2-hydroxy-1-methoxy4-(pentafluorophenylsulfonamido)benzene to produce 5-(pentafluorophenylsulfonamido)-2-methoxyphenyl phosphate.

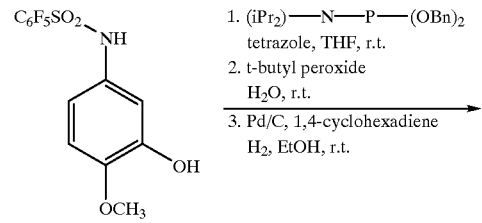

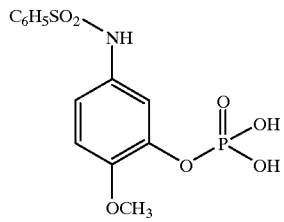

5-(Pentafluorophenylsulfonamido)-2-methoxyphenyl phosphate

2-Hydroxy-1-methoxy-4-(pentafluorophenylsulfonamido)benzene, prepared as described in WO 97/30677, (3.0 g, 8.2 mmol) and tetrazole (1.4 g, 19.7 mmol) were combined in 70 mL of dry THF and N,N-diisopropyl dibenzylphosphoramidite (2.8 mL, 8.2 mmol) was added. The reaction mixture was stirred at room temperature for 4.0 hours. At this point, the reaction mixture was cooled to 0° C. in an ice bath and 14% t-butyl peroxide (22 mL, 22.1 mmol) was slowly added. The reaction mixture was stirred for 0.5 hours, then 75 mL of a 10% $NaS_2O_3$ solution was added and the resulting mixture was stirred at room temperature for an additional 0.5 hours. THF was removed in vacuo, and the aqueous portion was extracted with EtOAc. The organic extract was dried over anhydrous MgSO$_4$ and the solvent was removed to provide a crude colorless oil that was purified by silica gel chromatography (3:7 EtOAc:hexanes as eluant). The product fractions were isolated and solvent was removed in vacuo to yield 3.9 g of a thick clear oil. $^1$H NMR (CDCl$_3$): δ 3.73 (s, 3H); 5.05 (t, J=9.1 Hz, 1H); 5.13 (s, 2H); 5.16 (s, 2H); 6.76 (d, J=11.8 Hz, 1H); 7.00 (d, J=11.8 Hz, 1H); 7.06 (s, 1H); 7.31 (s, 10H). ES MS: (M–H)=628.1

The intermediate phosphate diester (3.5 g, 5.6 mmol) was dissolved in 50 mL of dry ethanol. This was quickly poured into a flask containing 1.0 g of 10% palladium on carbon. Then 4.5 g (55.6 mmol) of cyclohexadiene was added and the reaction was allowed to stir at room temperature under a hydrogen atmosphere overnight. The palladium on carbon was removed by filtration through a layer of celite, and the solvent was removed in vacuo. The crude mixture was purified by reverse-phase HPLC. Removal of the solvents gave 1.13 g of the product phosphate as a white solid.

EXAMPLE 2

Assessment of Biological Activity.

. . . The ability of test compounds to arrest the growth of tumor cells in culture was evaluated using HeLa cells, derived from a human cervical adenocarcinoma, and obtained from the American Type Culture Collection (ATCC, Rockville, Md.). Cells were grown in culture in the usual way. Test compounds were dosed in triplicate at concentrations ranging from 5 nM to 50 μM, and the cellular growth rate was calculated by harvesting the cells after 72 hours of treatment and measuring their metabolic activity using an Alamar Blue assay (Biosource International, Camarillo, Calif.). The degree of metabolic activity in the culture is proportional to the number of living cells. See, Ahmed et al., J. Immunol. Methods 1994, 170, 211. The change in growth rate for cells treated with test compounds was normalized to the growth of untreated cells and a plot of normalized cellular growth vs. compound concentration was made. The concentration at which 50% growth inhibition (GI50) occurred was determined using a curve fitting program.

The following selected example displays potent cytotoxic activity in this assay.

| Compound | GI50 (nM) |
|---|---|
| Example 1 | 15 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating a disease state characterized by abnormally high levels of low density lipoprotein particles or cholesterol in the blood, which method comprises administering to a mammalian subject in need thereof a therapeutically effective amount of a composition comprising a compound of formula:

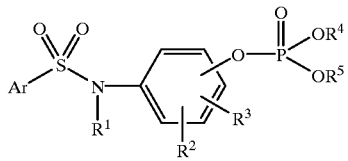

or a pharmaceutically acceptable salt thereof, wherein
$R^1$ is a member selected from the group consisting of hydrogen, $(C_1-C_6)$alkyl and $(C_1-C_6)$heteroalkyl;
$R^2$ and $R^3$ are each independently selected from the group consisting of hydrogen, halogen, $(C_1-C_8)$alkyl, $(C_1-C_8)$heteroalkyl, $-OR^{11}$ and $-NR^{11}R^{12}$, wherein $R^{11}$ and $R^{12}$ are each independently selected from the group consisting of hydrogen, $(C_1-C_8)$alkyl $(C_1-C_8)$heteroalkyl; or
$R^2$ and $R^3$, when attached to adjacent carbon atoms, can be linked together to form a fused 5-, 6- or 7-membered ring;
$R^4$ and $R^5$ are each independently selected from the group consisting of hydrogen, $(C_1-C_8)$alkyl, $(C_1-C_8)$heteroalkyl, aryl, heteroaryl, aryl$(C_1-C_4)$alkyl, aryl $(C_1-C_4)$ heteroalkyl, heteroaryl$(C_1-C_4)$alkyl and heteroaryl$(C_1-C_4)$heteroalkyl, and are optionally linked together to form a 5-, 6- or 7-membered ring; or
$R^4$ represents a single bond to the phenyl ring bearing the phosphoryl group and $R^5$ is selected from the group consisting of hydrogen, $(C_1-C_8)$alkyl, $(C_1-C_8)$ heteroalkyl, aryl, heteroaryl, aryl$(C_1-C_4)$alkyl, aryl $(C_1-C_4)$heteroalkyl, heteroaryl$(C_1-C_4)$ alkyl and heteroaryl$(C_1-C_4)$heteroalkyl; and
Ar is a substituted aryl group selected from the group consisting of:

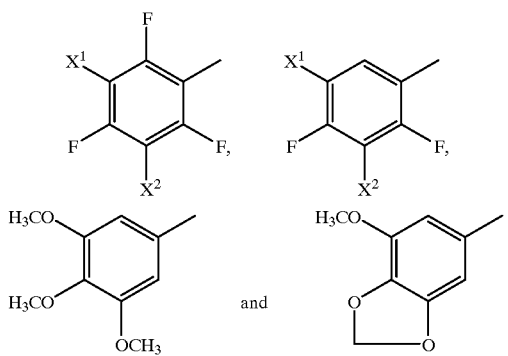

wherein
$X^1$ and $X^2$ are each independently selected from the group consisting of F, Cl and Br.

2. A method in accordance with claim 1, wherein Ar is selected from the group consisting of

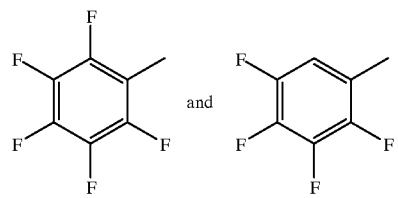

3. A method in accordance with claim 1, wherein Ar is pentafluorophenyl.

4. A method in accordance with claim 1, wherein Ar is 2,3,4,5-tetrafluorophenyl.

5. A method in accordance with claim 1, wherein Ar is 3,4,5-trimethoxyphenyl.

6. A method in accordance with claim 1, wherein Ar is 3-methoxy4,5-methylenedioxyphenyl.

7. A method in accordance with claim 1, wherein $R^1$ is hydrogen.

8. A method in accordance with claim 1, wherein $R^2$ is selected from the group consisting of hydrogen, $(C_1-C_3)$ alkyl and $(C_1-C_3)$alkoxy.

9. A method in accordance with claim 1, wherein $R^3$ is selected from the group consisting of hydrogen, $(C_1-C_3)$ alkyl, $-OR^{11}$ and $-NR^{11}R^{12}$, wherein $R^{11}$ and $R^{12}$ are each independently selected from the group consisting of hydrogen, $(C_1-C_3)$alkyl and $(C_1-C_3)$heteroalkyl.

10. A method in accordance with claim 1, wherein the disease state is hypercholesterolemia.

11. A method in accordance with claim 1, wherein the compound is administered orally.

12. A method in accordance with claim 1, wherein the compound is administered intravenously or intramuscularly.

13. A method in accordance with claim 1, wherein the disease state is pancreatitis.

14. A method in accordance with claim 1, wherein the disease state is hypercholesterolemia.

15. A method in accordance with claim 1, wherein the disease state is hyperlipoproteinemia.

16. A method of treating a disease selected from the group consisting of psoriasis, vascular restenosis, myocardial infarction and glomerular nephritis, which method comprises administering to a mammalian subject in need thereof a therapeutically effective amount of a composition comprising a compound of formula:

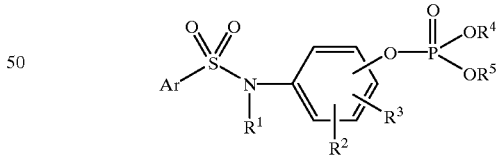

or a pharmaceutically acceptable salt thereof, wherein
$R^1$ is a member selected from the group consisting of hydrogen, $(C_1-C_6)$alkyl and $(C_1-C_6)$heteroalkyl;
$R^2$ and $R^3$ are each independently selected from the group consisting of hydrogen, halogen, $(C_1-C_8)$alkyl, $(C_1-C_8)$heteroalkyl, $-OR^{11}$ and $-NR^{11}R^{12}$, wherein $R^{11}$ and $R^{12}$ are each independently selected from the group consisting of hydrogen, $(C_1-C_8)$alkyl and $(C_1-C_8)$heteroalkyl; or
$R^2$ and $R^3$, when attached to adjacent carbon atoms, can be linked together to form a fused 5-, 6- or 7-membered ring;

23

R⁴ and R⁵ are each independently selected from the group consisting of hydrogen, $(C_1-C_8)$alkyl, $(C_1-C_8)$ heteroalkyl, aryl, heteroaryl, aryl$(C_1-C_4)$alkyl, aryl $(C_1-C_4)$ heteroalkyl, heteroaryl$(C_1-C_4)$alkyl and heteroaryl$(C_1-C_4)$heteroalkyl, and are optionally linked together to form a 5-, 6- or 7-rnembered ring; or R⁴ represents a single bond to the phenyl ring bearing the phosphoryl group and R⁵ is selected from the group consisting of hydrogen, $(C-C_8)$alkyl, $(C_1-C_8)$ heteroalkyl, aryl, heteroaryl, aryl$(C_1-C_4)$alkyl, aryl $(C_1-C_4)$heteroalkyl, heteroaryl$(C_1-C_4)$ alkyl and heteroaryl$(C_1-C_4)$heteroalkyl; and Ar is a substituted aryl group selected from the group consisting of:

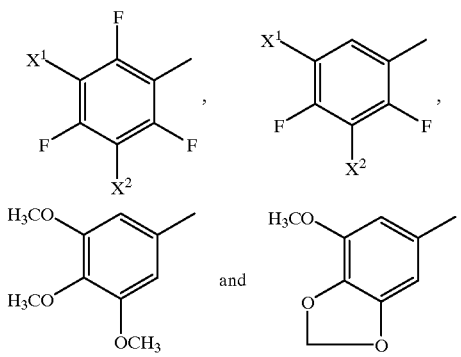

wherein $X^1$ and $X^2$ are each independently selected from the group consisting of F, Cl and Br.

17. A method in accordance with claim 16, wherein Ar is selected from the group consisting of

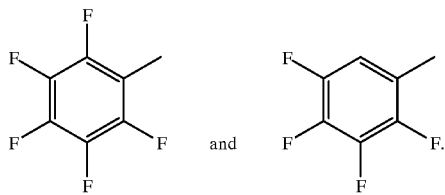

18. A method in accordance with claim 16, wherein Ar is pentafluorophenyl.

19. A method in accordance with claim 16, wherein Ar is 2,3,4,5-tetrafluorophenyl.

20. A method in accordance with claim 16, wherein Ar is 3,4,5-trimethoxylphynyl.

21. A method in accordance with claim 16, wherein Ar is 3-methoxy-4,5-methylenedioxyphenyl.

22. A method in accordance with claim 16, wherein R¹ is hydrogen.

23. A method in accordance with claim 16, wherein R² is selected from the group consisting of hydrogen, $(C_1-C_3)$ alkyl and $(C_1-C_3)$alkoxy.

24. A method in accordance with claim 16, wherein R³ is selected from the group consisting of hydrogen, $(C_1-C_3)$ alkyl, $—OR^{11}$ and $—NR^{11}R^{12}$, wherein $R^{11}$ and $R^{12}$ are each independently selected from the group consisting of hydrogen, $(C_1-C_3)$alkyl and $(C_1-C_3)$heteroalkyl.

25. A method in accordance with claim 16, wherein the compound is administered orally.

26. A method in accordance with claim 16, wherein the compound is administered intravenously or intramuscularly.

24

27. A method in accordance with claim 16, wherein the disease is psoriasis.

28. A method in accordance with claim 16, wherein the disease is vascular restenosis.

29. A method in accordance with claim 16, wherein the disease in myocardial infarction.

30. A method in accordance with claim 16, wherein the disease is glomerular nephritis.

31. A method of reducing levels of cholesterol or low density lipoproteins in blood, said method comprises administering to a mammalian subject in need thereof a therapeutically effective amount of a compositon comprising a compound of formula:

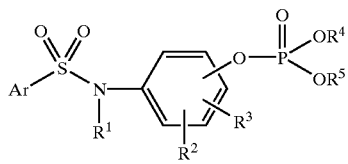

or a pharmaceutically acceptable salt thereof, wherein

R¹ is a member selected from the group consisting of hydrogen, $(C_1-C_6)$ alkyl and $(C_1-C_6)$heteroalkyl;

R² and R³ are each independently selected from the group consisting of hydrogen, halogen, $(C_1-C_8)$alkyl, $(C_1-C_8)$heteroalkyl, $—OR^{11}$ and $—NR^{11}R^{12}$, wherein $R^{11}$ and $R^{12}$ are each independently selected from the group consisting of hydrogen, $(C_1-C_8)$ alkyl and $(C_1-C_8)$heteroalkyl; or R² and R³ , when attached to adjacent carbon atoms, can be linked together to form a fused 5-, 6- or 7-membered ring;

R⁴ and R⁵ are each independently selected from the group consisting of hydrogen, $(C_1-C_8)$alkyl, $(C_1-C_8)$ heteroalkyl, aryl, heteroaryl, aryl$(C_1-C_4)$alkyl, aryl $(C_1-C_4)$ heteroalkyl, heteroaryl$(C_1-C_4)$alkyl and heteroaryl$(C_1-C_4)$heteroalkyl, and are optionally linked together to form a 5-, 6- or 7-rnembered ring; or R⁴ represents a single bond to the phenyl ring bearing the phosphoryl group and R⁵ is selected from the group consisting of hydrogen, $(C_1-C_8)$alkyl, $(C_1-C_8)$ heteroalkyl, aryl, heteroaryl, aryl$(C_1-C_4)$alkyl, aryl $(C_1-C_4)$heteroalkyl, heteroaryl$(C_1-C_4)$ alkyl and heteroaryl$(C_1-C_4)$heteroalkyl; and Ar is a substituted aryl group selected from the group consisting of:

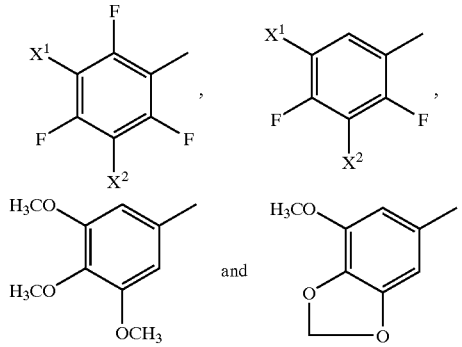

wherein $X^1$ and $X^2$ are each independently selected from the group consisting of F, Cl and Br.

32. A method in accordance with claim 31, wherein Ar is selected from the group consisting of

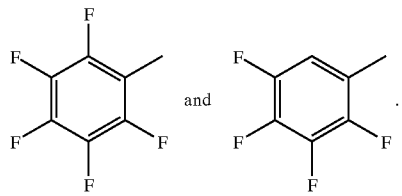

33. A method of inhibiting cell proliferation, comprising contacting a cell with a compound of the formula:

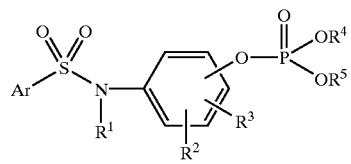

or a pharmaceutically acceptable salt thereof, wherein $R^1$ is a membered selected from the group consisting of hydrogen, $(C_1-C_6)$ alkyl and $(C_1-C_6)$heteroalkyl;

$R^2$ and $R^3$ are each independently selected from the group consisting of hydrogen, halogen, $(C_1-C_8)$alkyl, $(C_1-C_8)$heteroalkyl, —$OR^{11}$ and —$NR^{11}R^{12}$, wherein $R^{11}$ and $R^{12}$ are each independently selected from the group consisting of hydrogen, $(C_1-C_8)$ alkyl and $(C_1-C_8)$heteroalkyl; or $R^2$ and $R^3$, when attached to adjacent carbon atoms, can be linked together to form a fused 5-, 6- or 7-membered ring;

$R^4$ and $R^5$ are each independently selected from the group consisting of hydrogen, $(C_1-C_8)$alkyl, $(C_1-C_8)$heteroalkyl, aryl, heteroaryl, aryl$(C_1-C_4)$alkyl, aryl $(C_1-C_4)$ heteroalkyl, heteroaryl$(C_1-C_4)$alkyl and heteroaryl$(C_1-C_4)$heteroalkyl, and are optionally linked together to form a 5-, 6- or 7-rnembered ring; or $R^4$ represents a single bond to the phenyl ring bearing the phosphoryl group and $R^5$ is selected from the group consisting of hydrogen, $(C_1-C_8)$alkyl, $(C_1-C_8)$ heteroalkyl, aryl, heteroaryl, aryl$(C_1-C_4)$alkyl, aryl $(C_1-C_4)$heteroalkyl, heteroaryl$(C_1-C_4)$ alkyl and heteroaryl$(C_1-C_4)$heteroalkyl; and Ar is a substituted aryl group selected from the group consisting of:

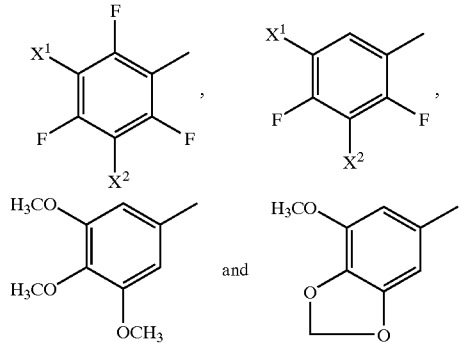

wherein $X^1$ and $X^2$ are each independently selected from the group consisting of F, Cl and Br.

34. A method in accordance to claim 33, wherein the contacting is in vitro.

35. A method in accordance to claim 33, wherein the contacting is in vivo.

36. A method in accordance to claim 33, wherein said compound interacts with tubulin to cause said inhibiting.

37. A method in accordance to claim 33, wherein said cell is an adenocarcinoma cell.

38. A method in accordance with claim 37, wherein said adenocarcinoma cell is a cervical adenocarcinoma cell.

* * * * *

UNITED STATES PATENT AND TRADEMARK OFFICE
CERTIFICATE OF CORRECTION

PATENT NO.    : 6,417,176 B2  
DATED         : July 9, 2002  
INVENTOR(S)   : Jonathan B. Houze It is certified that error appears in the above-identified patent and that said Letters Patent is hereby corrected as shown below:

Column 21,  
Line 28, please insert the word -- and -- between "$(C_1-C_8)$alkyl" and "$(C_1-C_8)$ heteroalkyl"

Column 22,  
Line 16, delete "trimethoxyphenyl" and replace therefore -- trimethoxylphenyl --.

Column 23,  
Line 6, delete "rnembered" and replace therefore -- membered --.  
Line 9, delete "$(C-C_8)$" and replace therefore -- $(C_1-C_8)$ --.  
Line 51, delete "trimethoxylphynyl" and replace therefore -- trimethoxylphenyl --.

Column 24,  
Line 40, delete "rnembered" and replace therefore -- membered --.

Column 25,  
Line 40, delete "rnembered" and replace therefore -- membered --.

Signed and Sealed this

Twenty-fifth Day of February, 2003

JAMES E. ROGAN  
*Director of the United States Patent and Trademark Office*